(12) United States Patent
Beer

(10) Patent No.: US 10,172,983 B2
(45) Date of Patent: Jan. 8, 2019

(54) SURGICAL SUCTION DEVICE

(71) Applicant: SURLUTIONS PTY LTD, Milton (AU)

(72) Inventor: Jason Keith Beer, Milton (AU)

(73) Assignee: SURLUTIONS PTY LTD, Milton, Queensland (AU)

( * ) Notice: Subject to any disclaimer, the term of this patent is extended or adjusted under 35 U.S.C. 154(b) by 554 days.

(21) Appl. No.: 14/650,366

(22) PCT Filed: Dec. 12, 2013

(86) PCT No.: PCT/AU2013/001456
§ 371 (c)(1),
(2) Date: Jun. 8, 2015

(87) PCT Pub. No.: WO2014/089627
PCT Pub. Date: Jun. 19, 2014

(65) Prior Publication Data
US 2015/0314050 A1 Nov. 5, 2015

(30) Foreign Application Priority Data
Dec. 14, 2012 (AU) .............................. 2012905491

(51) Int. Cl.
*A61M 1/00* (2006.01)
*A61B 17/3207* (2006.01)

(52) U.S. Cl.
CPC .......... *A61M 1/0023* (2013.01); *A61M 1/008* (2013.01); *A61M 1/0039* (2013.01);
(Continued)

(58) Field of Classification Search
CPC .. A61M 1/0023; A61M 1/008; A61M 1/0049; A61M 2205/8206;
(Continued)

(56) References Cited

U.S. PATENT DOCUMENTS 2,531,730 A * 11/1950 Henderson ........... A61C 17/043
285/343
2,674,777 A * 4/1954 Davis ...................... A01N 1/02
27/24.2

(Continued)

FOREIGN PATENT DOCUMENTS

| CN | 2183785 Y | 6/1999 |
|---|---|---|
| CN | 2326255 Y | 6/1999 |

(Continued)

*Primary Examiner* — Adam Marcetich
(74) *Attorney, Agent, or Firm* — Shay Glenn LLP

(57) ABSTRACT

A surgical suction device including: a) a housing defining an internal chamber and including: i) an inlet for receiving material extracted from a subject via a hollow tip including one or more suction openings for receiving the materials from a surgical site on the subject; and, ii) an outlet for coupling the housing to a suction source to allow material to be drawn therethrough; and, b) a mixing apparatus including one or more mixing members positioned inside the chamber for agitating material passing through the chamber from the inlet to the outlet in use to thereby prevent the material clogging the outlet.

19 Claims, 4 Drawing Sheets

(52) U.S. Cl.
CPC ............ *A61M 1/0049* (2013.01); *A61B 2017/320775* (2013.01); *A61M 2202/0014* (2013.01); *A61M 2205/103* (2013.01); *A61M 2205/8206* (2013.01)

(58) Field of Classification Search
CPC .... A61M 2205/103; A61M 2202/0014; A61M 1/0039; A61M 1/0082; A61M 1/0084; A61M 1/0037; A61B 2017/320775; A61B 17/32002; A61B 2017/320024; A61B 2017/320028; A61B 2017/320032; A61B 2017/00685; A61B 2217/005; A61B 17/320758; A61C 17/043; A61F 9/00763
See application file for complete search history.

(56) References Cited

U.S. PATENT DOCUMENTS

| | | | |
|---|---|---|---|
| 4,468,217 A | | 8/1984 | Kuzmick et al. |
| 4,649,919 A | * | 3/1987 | Thimsen .......... A61B 17/32002 30/133 |
| 4,729,763 A | | 3/1988 | Henrie |
| 4,790,812 A | * | 12/1988 | Hawkins, Jr. ......... A61B 17/221 604/22 |
| 4,857,046 A | * | 8/1989 | Stevens .................. A61B 1/12 604/22 |
| 4,886,492 A | | 12/1989 | Brooke |
| 5,114,399 A | | 5/1992 | Kovalcheck |
| 5,571,081 A | * | 11/1996 | Adhoute ............. A61M 1/0084 604/269 |
| 6,143,009 A | | 11/2000 | Shiber |
| 6,206,898 B1 | | 3/2001 | Honeycutt et al. |
| 6,406,454 B1 | | 6/2002 | Hajianpour |
| 6,767,353 B1 | | 7/2004 | Shiber |
| 8,790,349 B2 | | 7/2014 | Takahashi |
| 9,135,763 B2 | | 9/2015 | Gupta |
| 2002/0138020 A1 | * | 9/2002 | Pflueger ............. A61B 10/0266 600/562 |
| 2002/0188280 A1 | * | 12/2002 | Nguyen ......... A61B 17/320016 604/542 |
| 2003/0078586 A1 | * | 4/2003 | Shapira ................ A61B 10/025 606/80 |
| 2005/0256464 A1 | * | 11/2005 | Pallas ............ A61B 17/320708 604/319 |
| 2006/0058584 A1 | * | 3/2006 | Hirata ................ A61B 1/00177 600/179 |
| 2006/0106353 A1 | * | 5/2006 | Geneve ................ A61C 1/0076 604/319 |
| 2007/0055282 A1 | * | 3/2007 | Muschler ........... A61B 10/0233 606/92 |
| 2008/0004647 A1 | * | 1/2008 | To ......................... A61B 17/22 606/159 |
| 2008/0183125 A1 | * | 7/2008 | Issa ...................... A61F 11/006 604/26 |
| 2008/0208230 A1 | | 8/2008 | Chin et al. |
| 2009/0306669 A1 | * | 12/2009 | Takahashi ........... A61C 1/0076 606/80 |
| 2011/0112515 A1 | | 5/2011 | Stiehl et al. |
| 2011/0275327 A1 | * | 11/2011 | Lint .................... A61C 1/0015 455/66.1 |
| 2011/0301634 A1 | | 12/2011 | Aklog et al. |

FOREIGN PATENT DOCUMENTS

| | | |
|---|---|---|
| CN | 2358907 Y | 1/2000 |
| CN | 201806977 U | 4/2011 |
| GB | 1505007 A | 3/1978 |
| GB | 2367750 A | 4/2002 |
| GB | 2403907 B | 6/2006 |
| GB | 2494730 A | 3/2013 |

* cited by examiner

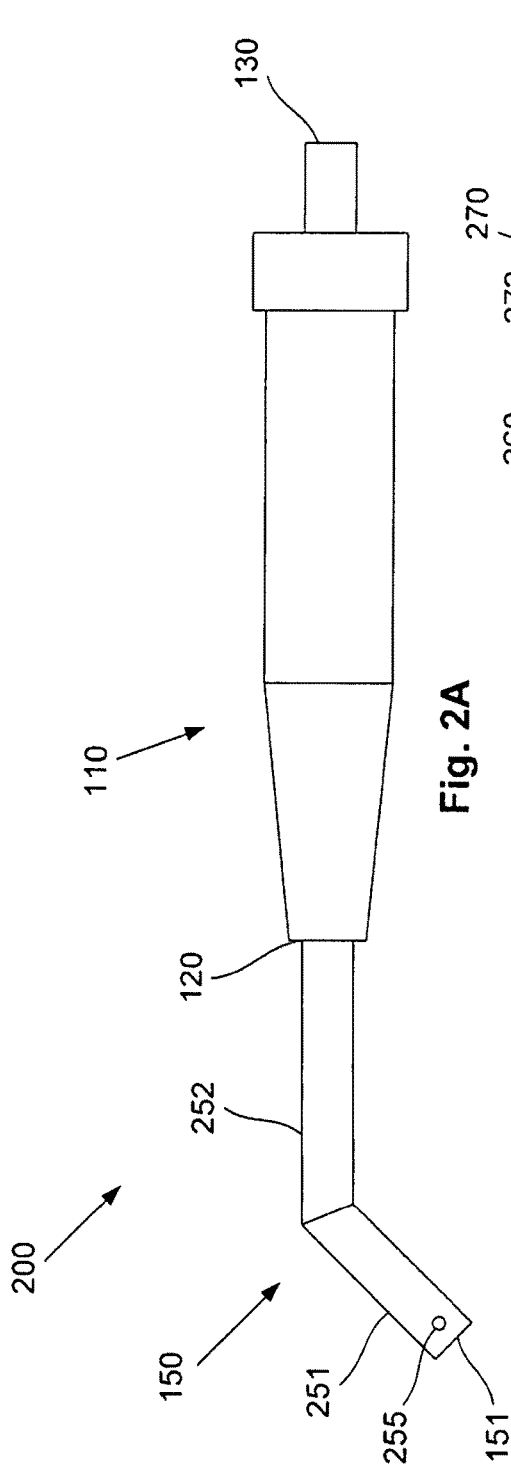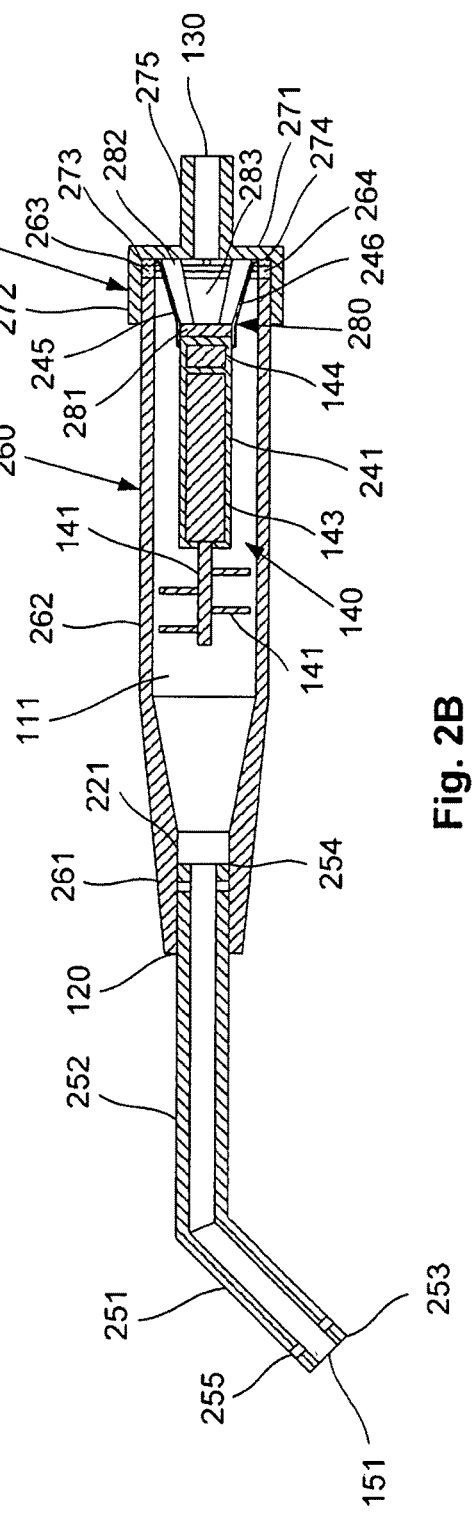

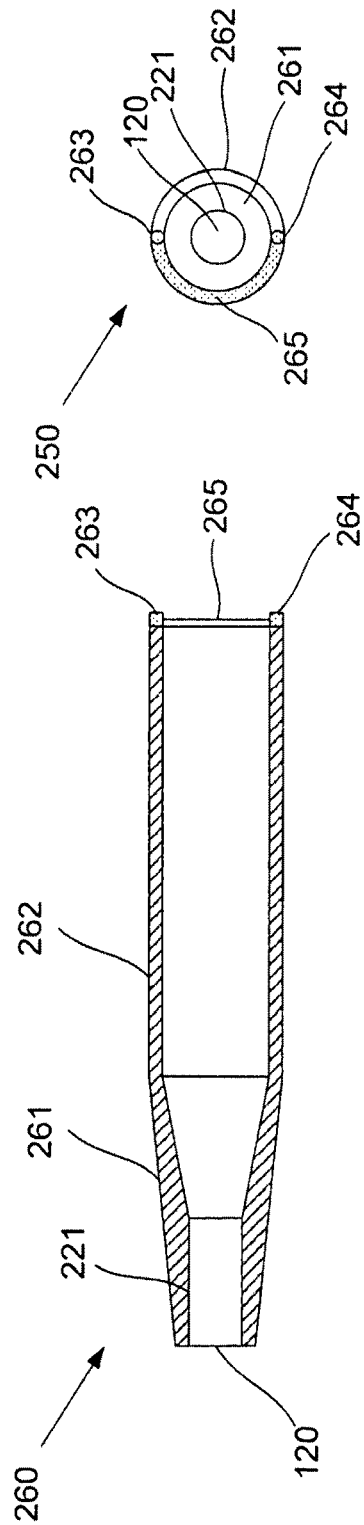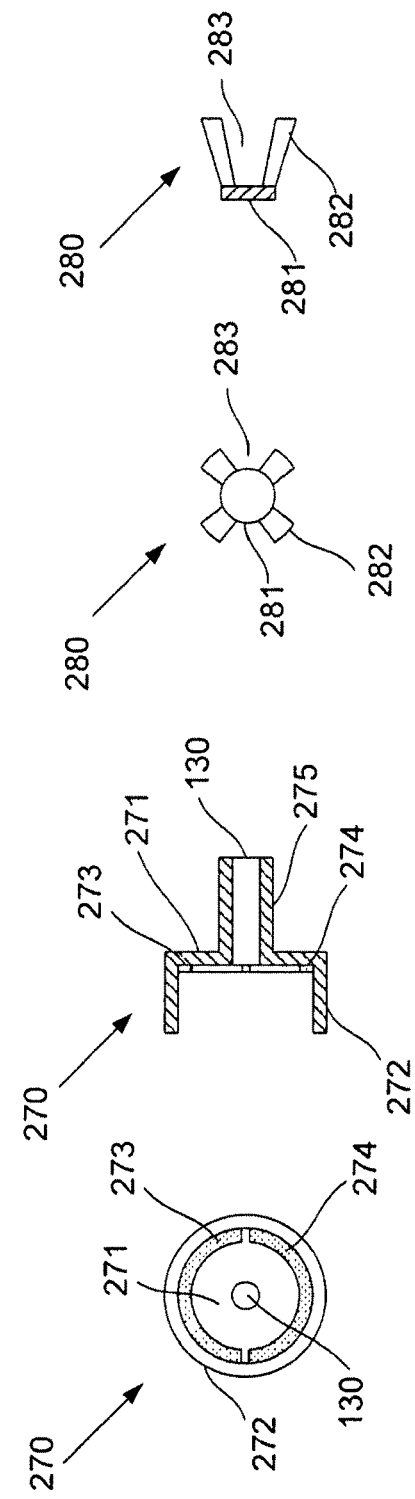

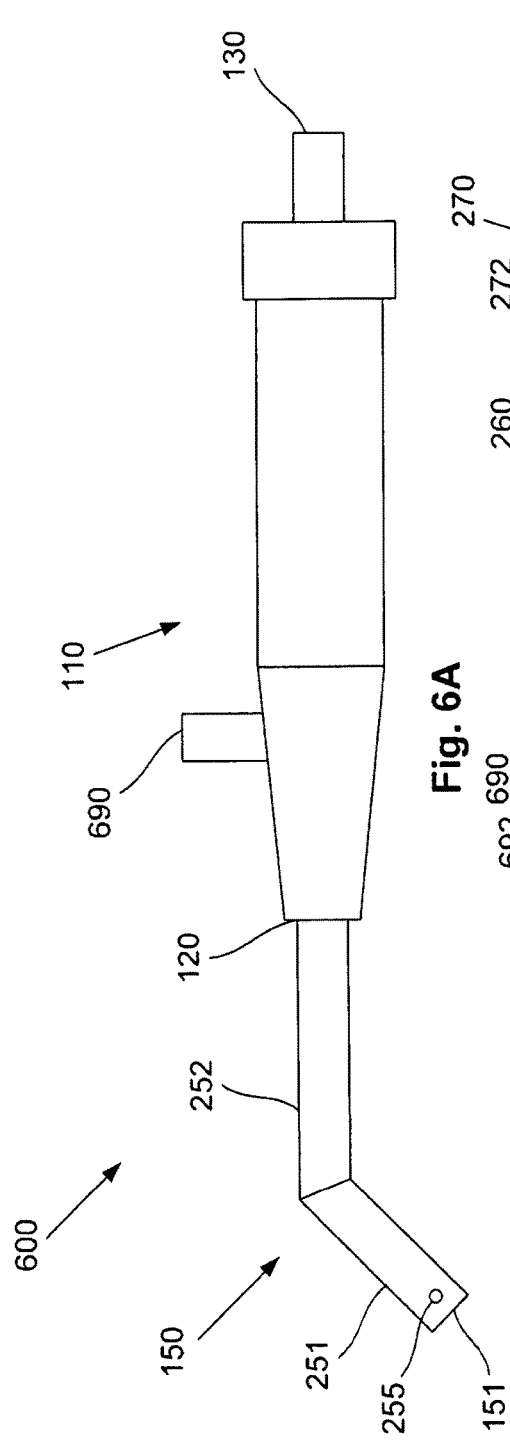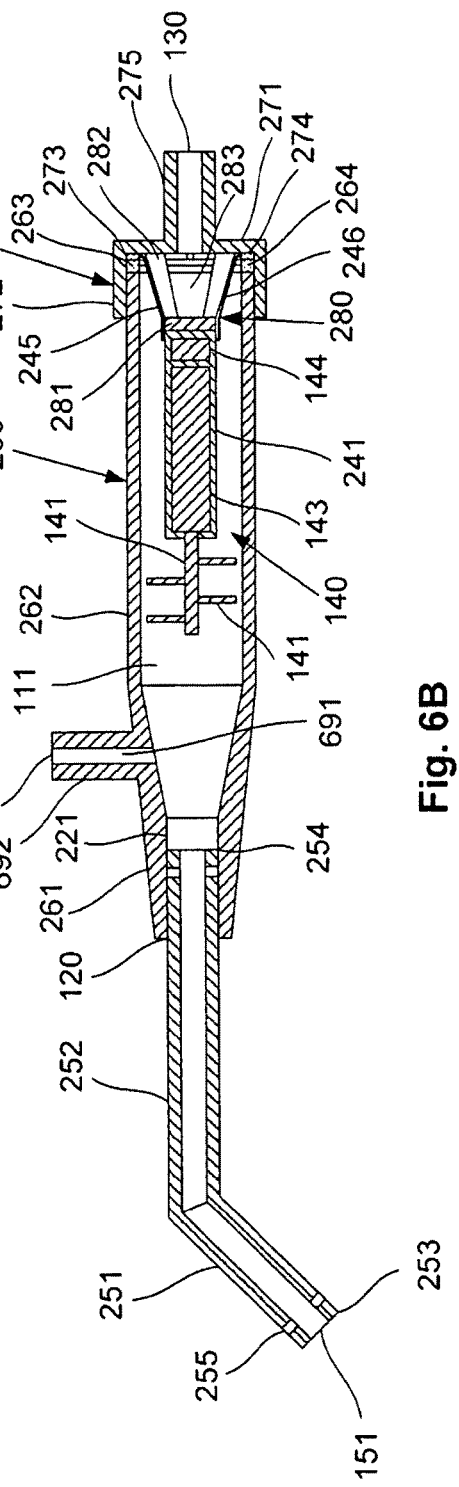
Fig. 6A
Fig. 6B

SURGICAL SUCTION DEVICE

BACKGROUND OF THE INVENTION

The present invention relates to a surgical suction device.

DESCRIPTION OF THE PRIOR ART

The reference in this specification to any prior publication (or information derived from it), or to any matter which is known, is not, and should not be taken as an acknowledgment or admission or any form of suggestion that the prior publication (or information derived from it) or known matter forms part of the common general knowledge in the field of endeavour to which this specification relates.

A range of surgical procedures will require the removal of fluids and tissue material from a surgical site of a patient's body. The removal is frequently carried out using suction. Surgical suction devices may include a suction tip coupled to suction tubing which is in turn coupled to a wall suction unit or the like. Some examples of existing suction tips include an elongated cannula for drawing the fluids or tissues from the surgical site into a suction handle which also provides for connection to the suction tubing. The cannula may be exchangeable to allow different shapes to be used depending on the particular application.

One problem commonly encountered in surgical suction devices is clogging of the suction tip or suction tubing, which can result in a reduction or loss of suction. Clogs may occur due to solid particles obstructing flow through the suction tip or suction tubing. Some existing suction devices include a removable filter for trapping solid particles in a way that prevents obstruction. Such a filter may be provided within a cavity inside the suction handle.

However, suction tips may still become clogged due to clotted blood and soft tissues, even when a filter is used. Clogs can develop over extended periods of use even when solid particles are not being removed from the body, due to the accumulation of clotted blood and/or soft tissue matter. Whilst a filter can be removed for cleaning or replacement, this will nevertheless further interrupt the availability of suction during the procedure.

A number of developments in surgical suction devices have focussed on improving the configuration of filters to allow longer periods of use between cleaning or replacement of the filter and/or to facilitate cleaning or replacement of the filter which with a faster turnaround time or without requiring an interruption to suction.

U.S. Pat. No. 4,886,492 discloses a surgical suction tip having a tubular body portion with a hollow tip portion and a hollow filter member within the body portion which defines an annular chamber. A plurality of apertures in the filter member connects the interior of the filter member with the annular chamber. Waste material flows from the tip portion into the hollow interior of the filter member and then to the annular chamber and ultimately to connected suction tubing. Whilst this configuration can be effective in delay clogging due to an accumulation of solid particles by providing numerous apertures which must each be blocked before the suction tip becomes completely clogged, in practice the relatively small apertures have been found to be prone to clogging due to clotted blood and soft tissues and thus frequent cleaning or replacement of the filter may still be required.

GB-2403907 discloses a filtered surgical suction tip comprising a tubular body with a side mounted fluid outlet and a filter which is inserted or removed via the rear of the body without the need to disconnect the suction tubing. The filter may be removed from the body for changing or unblocking without the need to disconnect tubing or remove a cap. Whilst this arrangement seeks to reduce interruptions to suction by facilitating simplified filter removal and replacement, this does not significantly impact on the actual frequency of clogging.

U.S. Pat. No. 6,406,454 discloses a suction probe system for cleaning debris from a surgical site including a probe tip, a filter unit in fluid communication with the probe tip, and a suction source in fluid communication with the filter unit. The filter unit includes a cylindrical filter having an inner chamber attached to the suction source and an outer surface which accumulates debris particles too large to pass through holes within the cylindrical filter. The filter unit also includes a slider having an open-ended cylinder which is slid along the outside of the cylindrical filter to remove accumulated debris particles and to push these debris particles into a reservoir within the filter unit. This may allow some clogs to be cleared without interrupting suction by mechanically removing debris particles from the filter as required, but may have limited effectiveness in preventing clogs due to accumulation of clotted blood or soft tissues.

Although the examples of the prior art discussed above can extend the period of operation before the onset of clogging or reduce the operation impact of clogging, none of these effectively address the problem of clogging due to clotted blood or soft tissues. Accordingly, there remains a need for a surgical suction device having an improved resistance to clogging due to clotted blood or soft tissues.

SUMMARY OF THE PRESENT INVENTION

In a broad form the present invention seeks to provide a surgical suction device including:
 a) a housing defining an internal chamber and including:
  i) an inlet for receiving material extracted from a subject via a hollow tip including one or more suction openings for receiving the materials from a surgical site on the subject; and,
  ii) an outlet for coupling the housing to a suction source to allow material to be drawn therethrough; and,
 b) a mixing apparatus including one or more mixing members positioned inside the chamber for agitating material passing through the chamber from the inlet to the outlet in use to thereby prevent the material clogging the outlet.

Typically the tip is attached to the inlet.

Alternatively the tip can be coupled to the inlet via a suction tube.

Typically the housing defines a handle for the surgical suction device.

Typically the outlet includes a connector for connection to the suction source.

Typically the mixing apparatus is configured to rotate the mixing members.

Typically the mixing apparatus includes:
 a) a shaft for mounting the one or more mixing members; and,
 b) a motor for rotationally driving the shaft.

Typically the one or more mixing members are at least one of:
 a) radially extending protrusions;
 b) blades; and,
 c) a helical wire.

Typically the motor is an electric motor and the mixing apparatus includes a battery for electrically powering the motor.

Typically the motor and the battery are provided together within a sealed housing.

Alternatively the battery can be positioned outside the chamber and connected to the motor by wiring.

Typically the surgical suction device includes a controller for controlling the supply of electrical power to the motor from the battery.

Typically the controller includes a switch positioned outside the housing for manual operation by a user.

Typically the controller is configured to periodically apply electrical power to the motor.

Typically the mixing apparatus includes an orientation sensor, the controller being configured to apply power to the motor when the surgical suction device is in a predetermined orientation.

Typically the tip is removably attachable to the housing.

Typically the housing is formed from a main housing part including the inlet and a base part including the outlet.

Typically the main housing part and the base part are screwingly connected together.

Typically the mixing apparatus includes an electrical circuit for powering the motor, the electrical circuit being open except when the main housing part and the base part are screwingly connected together.

Typically respective portions of the main housing part and the base part each include pairs of electrical contacts which are brought into engagement to close the electrical circuit when the main housing part and the base part are screwingly connected together.

Typically the surgical suction device includes a support structure attached to the housing and positioned inside the chamber for supporting the mixing apparatus.

Typically the support structure includes a mounting platform supported inside the chamber by one or more supporting members attached to the housing, the mixing apparatus being mounted on the mounting platform.

Typically the support structure includes a plurality of supporting members, the supporting members being spaced apart to define gaps for allowing material to pass through the gaps.

Typically the tip is for insertion into a surgical site to thereby allow material to be received from the surgical site, and the housing is attached to the tip so that the housing is positioned outside the surgical site and proximate to the subject in use.

Typically the surgical suction device includes an inflow port for allowing a fluid to be drawn into the chamber via the inflow port in use.

Typically the inflow port is configured to allow a fluid source to be connected to the inflow port to thereby supply the fluid.

Typically the inflow port defines a fluid conduit through a wall of the housing.

Typically the inflow port is formed integrally with the housing.

Typically the surgical suction device includes a valve for controlling a flow of fluid via the inflow port.

BRIEF DESCRIPTION OF THE DRAWINGS

An example of the present invention will now be described with reference to the accompanying drawings, in which:—

FIG. 2A is a schematic side view of a second example of a surgical suction device;

FIG. 2B is a schematic cross-section view of the surgical suction device of FIG. 2A;

FIG. 3A is a schematic cross-section view of a main housing part of the surgical suction device of FIG. 2A;

FIG. 3B is a schematic end view of the main housing part of FIG. 3A;

FIG. 4A is a schematic end view of a base part of the surgical suction device of FIG. 2A;

FIG. 4B is a schematic cross-section view of the base part of FIG. 4A;

FIG. 5A is a schematic end view of a support part of the surgical suction device of FIG. 2A;

FIG. 5B is a schematic cross-section view of the support part of FIG. 5A;

FIG. 6A is a schematic side view of a third example of a surgical suction device; and, FIG. 6B is a schematic cross-section view of the surgical suction device of FIG. 6A.

DETAILED DESCRIPTION OF THE PREFERRED EMBODIMENTS

Figure 1:
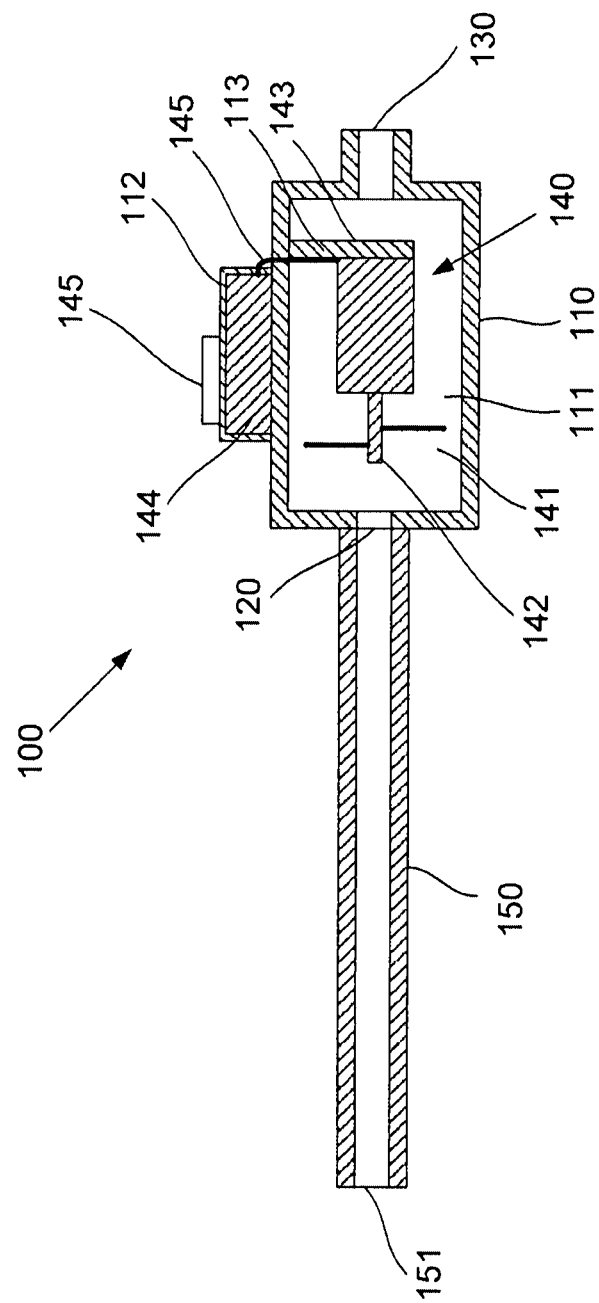
FIG. 1 is a schematic cross-section view of an example of a surgical suction device.

An example of a surgical suction device 100 will now be described with reference to FIG. 1.

The surgical suction device 100 generally includes a housing 110 defining an internal chamber 111. The housing includes an inlet 120 and an outlet 130. The inlet 120 is for receiving material extracted from a subject via a tip 150 which includes one or more suction openings 151. The outlet 130 is for coupling the housing 110 to a suction source (not shown) to allow material to be drawn therethrough.

When the outlet 130 is coupled to the suction source, for example via suction tubing, material can be extracted from a surgical site of the subject by being drawn into the one or more suction openings 151 and conveyed via the tip 150 to the inlet 120 of the housing 110 by suction. The material extracted from the subject can then pass through the chamber 111 from the inlet 120 to the outlet 130.

It will be appreciated that the materials may be biological materials or surgical debris which may produced during a surgical procedure. For example, the material may include blood, clotted blood, saliva, other bodily fluids, tissues, bone fragments, surgical irrigation fluids, cement, and the like.

The surgical suction device 100 further includes a mixing apparatus 140 including one or more mixing members 141 positioned inside the chamber 111 for agitating material passing through the chamber 111 from the inlet 120 to the outlet 130, to thereby prevent the material clogging the outlet 130.

As the mixing members 141 agitate the material in the chamber 111, this causes different components of the materials to move relative to one another, thus increasing the homogeneity of the materials and thereby substantially reducing the likelihood of accumulation of solid or gelatinous components of the materials which tend to cause clogs within conventional surgical suction devices. This agitation action further acts to prevent clotting of blood.

Depending on the particular materials removed from the surgical site, the mixing members 141 may be used to homogenize, mix, blend, liquidize, emulsify, chop or break down components of the materials.

For example, in surgical procedures where blood is removed from the surgical site, clotted blood and other debris may accumulate within the chamber 111, and without intervention this could result in clogging of the surgical suction device 100. However, the mixing members 141 can be used to emulsify the clotting blood to help to maintain the material extracted from the subject in a generally liquid state to allow the material to exit the chamber 111 by passing through the outlet 130 with a greatly reduced risk of blockages.

In another example, removed soft tissues in material extracted from the subject may be chopped or broken down into smaller particles by the mixing members 141 and distributed more evenly within the material stream as it passed through the chamber 111 to thereby prevent undesirable accumulations of the soft tissues within the chamber 111. Even solid particles in the material which cannot be broken down can be distributed more evenly in the material stream due to movement within the materials that will be induced by the agitation caused by the mixing members 141, to thus prevent blockages which might otherwise occur if these were allowed to settle in the chamber 111.

In view of the above, it will be appreciated that the above described surgical suction device 100 arrangement can assist in ensuring that suction remains available throughout a surgical procedure, by reducing the occurrence of clogs or blockages and thus maintaining the patency of the surgical suction device 100 and any upstream components used to couple the surgical suction device 100 to the suction source.

Suitable suction sources may include wall suction units or portable suction pumps of the types commonly employed in hospitals for use with conventional suction devices. The outlet 130 may include a connector configured for connection to the suction source. The surgical suction device 100 will be typically be connected to the suction source using tubing, commonly formed from a flexible transparent material, but any suitable means of connection may be used.

A container may be provided with the suction source or connected at an intermediate position between the surgical suction device 100 and the suction source to collect materials which have been removed from the surgery site and conveyed towards the suction source. Persons skilled in the art will appreciate that a range of common configurations can be used to provide the suction source and connect this to the surgical suction device 100 whilst allowing suitable operation.

It will be appreciated that the tip 150 used to extract material from the subject can have a range of different configurations. The tip 150 may be provided in the form of an elongate hollow member, which can be provided in fluid communication with the inlet 120. The tip 150 may be formed as a rigid or flexible component and a variety of tip shapes may be used depending on the nature of the surgical site, to allow material to be efficiently and safely extracted from the subject. In one example, such as shown in FIG. 1, the tip 150 may be directly coupled to the inlet 120. Alternatively, the tip 150 may be coupled to the inlet via a suction tube.

The tip 150 may be removable allowing different types of tip 150 to be fitted to the housing 110, for example depending on the intended use of the suction device 100. This allows the suction device 100 to be provided as part of a kit, with different tips, allowing a single kit to be used in a wide range of different procedures. Alternatively, the tip 150 may be integrally formed as part of the housing 110.

In one example, the housing 110 may define a handle for the surgical suction device 100. For example, an external profile of the housing 110 may be selected so that a user can grip the housing 110 in one hand and thus hold and move the surgical suction device 110 as required. It will be appreciated that if the tip 150 is rigidly attached to the housing, the tip 150 may be moved by the user by gripping and moving or otherwise manipulating the housing 110. This can allow a user to position the one or more suction openings 151 of the tip 150 within a surgical site of the subject whilst holding the housing 110 outside of the surgical site.

In the present example, the mixing apparatus 142 is configured to rotate the mixing members 141 to thereby cause them to agitate the material passing through the chamber 111. As depicted in FIG. 1, the mixing apparatus 140 may include a shaft 142 for mounting the one or more mixing members 141 and a motor 143 for rotationally driving the shaft 142. Accordingly, the mixing members 141 will rotate when the motor 143 is activated. In the present example, the motor 143 is positioned inside the chamber 111 along with the mixing members 141. However, it will be appreciated that alternative embodiments may position the motor 143 outside the chamber 111 and have the shaft 142 pass through a wall of the housing 110 so that the mixing members 141 positioned inside the chamber 111 can still be driven by the motor 143.

Suitable mixing members 141 may be provided in a range of different configurations, which may depend on the type of material to be extracted from the subject. For example, the mixing members 141 may include one or more radially extending protrusions or blades mounted on the shaft 142. Any number of blades may be used, depending for example on the particular intended use, and the likelihood of blocking associated with the particular procedure being performed.

Blades having a sharp cutting surface may be particularly suitable for chopping or breaking down tissues in the material, although blunt protrusions may provide sufficient agitation. Alternatively, a helical wire may be mounted on the shaft 142 to also provide suitable agitation of material in the chamber 111.

The mixing members 141 may be suitably formed from metal or a relatively hard plastic. The shape and construction of the mixing members 141 should be selected to ensure that they can rotate through typical extracted materials without excessive deformations, although it may also be desirable to use mixing members 141 which have some flexibility to allow the mixing members 141 to deflect rather than break in the event of an impact with a solid particle such as a bone fragment.

The motor 143 may be an electric motor and thus may be powered by an electrical power source, although it will be appreciated that other types of motors such as pneumatic motors may be used. In one example, the motor 143 may be configured to operate when connected to the suction source. For instance, the motor may include a turbine positioned between an air inlet and a suction outlet so that the turbine rotates as air is drawn into the air inlet past the turbine under suction. The turbine will in turn cause the shaft 142 and mixing members 141 to rotate.

In the case of an electric motor, any electrical power source may be used, such as a connection to an external power supply such as a wall power outlet. Conveniently, the mixing apparatus 140 may include a battery 144 for electrically powering the motor 143 without requiring an external power connection. The battery 144 may be connected to the motor 143 by electrical wiring 145. In the example shown in FIG. 1, the battery 144 is provided in a battery compartment 112 attached to the housing 110 outside the chamber 111 and thus is separated from the motor 143. Accordingly, the wiring 145 may be passed through a suitably sealed aperture in the housing 110, or, in the even the housing 110 is formed from multiple parts, electrical contacts may be provided at a joint between housing parts to allow an electric circuit to be formed when parts are joined together to form the complete housing.

In this example, the mixing apparatus 140 includes a switch 146 which is connected to the wiring 145 and positioned outside the housing 110 such that the switch 146 can be manually operated by a user. In this case the switch 146 is mounted on the protruding battery compartment 112.

When the switch 146 is operated by a user of the surgical suction device 100, the motor 143 can be selectively activated or de-activated. The switch 146 can thus allow the mixing members 141 to be rotated as required to prevent clogging of the surgical suction device 100. For example, the surgical suction device 100 may be normally used without activating the motor 143, and when clotted blood begins to accumulate inside the chamber 111, the switch 145 may be operated by the user to activate the motor 143 and cause rotation of the mixing members 141 to emulsify the clotted blood and hence reduce the likelihood of clogging.

Whilst a switch 145 is provided in this example, alternative means of controlling the activation of the motor 143 may be used, and further examples will be discussed in due course.

Structural components of the surgical suction device 100 may be formed from plastic materials suitable for medical applications, such as Polyvinyl Chloride or Styrene Acrylnitril. Preferably the material used to form at least the housing 110 will be substantially transparent to allow the user to observe material being conveyed through the chamber 111. Accordingly, the user can monitor the amount of accumulated clotted blood, tissues and other material which may potentially clog the surgical suction device 100 and activate the motor 143 as appropriate.

Components of the mixing apparatus 140 which are positioned in the chamber 111 may be supported inside the chamber 111 using additional support structure connected to the housing 110 inside the chamber 111. In this example, a support flange 113 extends into the chamber 111 from a side wall of the housing 110 and the motor 143 is mounted on the support flange 113. The support structure should be configured to allow material to pass through the chamber 111 from the inlet 120 to the outlet 130 without significant obstruction. Alternative support structure configurations will be described in due course.

A further example of a surgical suction device 200 will now be described with reference to FIGS. 2A and 2B, to highlight further optional features, with similar reference numerals being used to identify similar features to the previous example.

In this case, the tip 150 is provided as a hollow, generally tubular member, which is removably attachable to the housing 110. In this example, the tip 150 has a rigid construction and includes a first portion 251 and a second portion 252 oriented at an angle to the first portion 251. This angled configuration can allow the tip 150 to be introduced into surgical sites whilst the housing 110 is held by the user in a natural position.

The tip 150 may be reversible in that similar openings 151 are provided at each end 253, 254 of the tip 150, such that either end 253, 254 may be connected to the housing 110. In this example, the first and second portions 251, 252 of the tip 150 have different lengths, and thus reversal of the tip 150 can allow different depths of insertion of the tip 120 into a surgical site. The tip 150 is preferably formed from a relatively rigid, transparent plastic, such as Polyvinyl Chloride.

The tip 150 is coupled to the housing 110 by inserting an end 253, 254 into a cylindrical receptacle 221 formed in the housing 110, which communicates with the chamber 111 and thus effectively defines the inlet 120. The respective outer diameter of the end 253, 254 of the tip 150 and the receptacle 221 in the housing 110 may be selected so that the end 253, 254 of the tip 150 can be inserted into the receptacle 221 with a push fit, allowing the tip 150 to be firmly retained by the receptacle 221 in use, yet easily disassembled as required. However, it will be appreciated that other connection techniques, such as clip-fit, friction-fit or interference fit can be used.

As can be seen in FIG. 2A and the corresponding cross-section view of FIG. 2B, each end 253, 254 of the tip 150 includes a main opening 151 along with a plurality of secondary openings 255 adjacent the respective end 253, 254. In this example, four secondary openings 255 are formed as holes through the sidewalls of the tip 150. The secondary openings 255 can help to reduce the risk of trauma to soft tissue if drawn into the main opening 151, as pressure can be relieved via the secondary openings 255 in the event the main opening 151 becomes obstructed.

In this example, the housing 110 is formed from two separate parts which are joined together to collectively define the internal chamber 111. In particular, the housing 110 is formed from a main housing part 260 and a base part 270.

Further details of the main housing part 260 can be seen in FIGS. 3A and 3B. The main housing part 260 includes an end portion 261 which provides the receptacle 221 for allowing connection of the tip 150 and an elongate generally cylindrical portion 262 which defines sidewalls of the chamber 111. The cylindrical portion 262 may form a handle of the housing 110 which is gripped by a user in use. Accordingly, the cylindrical portion 262 may include external features for improving grip, such as finger indents, ridges, dimples or the like.

Further details of the base part 270 can be seen in FIGS. 4A and 4B. The base part 270 includes a cap portion 271 for enclosing the end of the chamber 111 opposite the receptacle 221. A skirt portion 271 extends from a cap portion 272 for allowing the base part 270 to be connected to the cylindrical portion 262 of the main housing part 260. The base part 270 also includes a connector 275 for allowing the suction source to be coupled to the outlet 130 which is provided in the base part 270.

In the present example the main housing part 260 and the base part 270 are screwingly connectable to one another via corresponding threaded portions provided on an external surface of the cylindrical portion 262 of the main housing part 260 and an internal surface of the skirt portion 272 of the base part 270. Alternatively, the main housing part 260 and the base part 270 may be connected by a push fit through suitable dimensioning and/or material selection, or by any other suitable technique, such as friction-fit or interference-fit for providing a sealed connection. Each of the main housing part 260 and the base part 270 will preferably be formed from a transparent plastic material to allow the material passing through the chamber 111 to be observed by a user, and typically both parts will be formed from the same material, although this is not essential.

As discussed above, at least the mixing members 141 of the mixing apparatus 140 are positioned in the chamber 111. In this example, the shaft 142, the motor 143 and the battery 144 are each positioned inside the chamber 111. Specifically, the motor 143 and the battery 144 are provided together within a single enclosure 241. The shaft 142 protrudes from an aperture formed in the enclosure 241 to allow the mixing members 141 to be located in an appropriate position for agitating materials passing through the chamber 111.

In this example, the enclosure 241 is supported inside the chamber 111 by a support part 280 which is connected to the base part 270. Further details of the support part 280 can be seen in FIGS. 5A and 5B. The support part 280 provides a mounting platform 281 upon which the housing 241 is mounted, which is in turn supported inside the chamber 111 by one or more supporting members 282.

The supporting members 282 are spaced apart to define gaps 283 to allow material to flow from the chamber 111 past the support part 270 and to the connector 130. The gaps 283 should define openings that are at least as large as main opening 151 of the tip 150 to prevent any particles that can be extracted from the subject from becoming blocked in a gap 283.

It will be appreciated that any suitable alternative configuration of support structure for supporting the enclosure 241 or any components of the mixing apparatus 140 positioned inside the chamber 111 can be used. In one example, components of the mixing apparatus 140 may be directly attached to the housing 110 thus eliminating the need for discrete support structure components.

Since the battery 144 is provided with motor 143, electrical power can be directly supplied from the battery 144 to the motor 143. However, the mixing apparatus 140 will preferably also include some means for allowing the user to determine when the motor 143 should be activated. A control arrangements including a switch 146 similar to that described above with reference to FIG. 1 may be used. However it is noted that in this example it is not necessary to pass wiring outside the housing 110 and therefore an external switch 146 may require otherwise unnecessary wiring routes to be provided. Instead of a switch 146, the mixing apparatus 140 may include an electrical circuit for powering the motor 143 which is configured to be always open except when the main housing part 260 and the base part 270 are connected.

In the present example, respective portions of the main housing part 260 and the base part 270 each include pairs of electrical contacts 263, 264 and 273, 274 which are respectively brought into engagement to close the electrical circuit when the main housing part 260 and the base part 270 are screwingly connected together. An electrical conductor 265 spans between the electrical contacts 263, 264 of the main housing part 260 to complete the electrical circuit connecting the motor 143, the battery 144, and the contacts 273, 274 of the base part 260 which are connected to the components inside the enclosure 241 by wires 245, 246.

It may also be generally desirable to provide other means of controlling supply of electrical power from the battery 144 and hence the activation of the motor 143. Whilst a switch 146 or arrangement of contacts 263, 264, 271, 272 can provide a simplified form of controller, in other examples a controller unit (not shown) may be embedded within the housing and provided in an electrical circuit connecting the battery 144 to the motor 143.

A range of different controller unit configurations may be used. For instance, the mixing apparatus 140 may include one or more sensors and the controller unit may be configured to process inputs from the one or more sensors in order to determine whether the motor 143 should be activated.

In one example, the mixing apparatus 140 may include an orientation sensor and the controller may be configured to apply power to the motor 143 when the surgical suction device 200 is held in a predetermined orientation. For instance, the motor 143 may remain inactive whilst the surgical suction device 200 is held with the tip 120 extending generally horizontally or downwardly from the housing 110, but when the surgical suction device 200 is held with the tip 120 extending upwardly the motor 143 may be activated. Accordingly, the user can cause the motor 143 to be activated on demand by temporarily reorienting the surgical suction device 200, such as when an accumulation of potentially clogging material is observed within the chamber 111 during use.

In other examples, the mixing apparatus 140 may include a sensor for detecting the presence or movement of material within the chamber 111, such as a suitably configured flow sensor or pressure sensor. Thus, the controller may be configured to only activate the motor 143 when waste materials are detected, to thereby prevent rotation of the mixing members 141 when no materials are within the chamber 111 to be mixed. Other forms of sensing, such as motion sensing or the like may also be used.

Additionally, the controller can be configured to activate the mixing members 141 for a predetermined amount of time. This can be performed periodically, or alternatively in response to sensing of movement or the like. For example, if movement is sensed, the motor 143 can be activated for 10 seconds, or for a period of time corresponding to whilst movement is being sensed, and for an additional time period of 10 seconds, to ensure the material is suitable agitated. Alternatively, the motor 143 can be activated and remain active throughout the entire procedure, stopping only once the battery runs out, or once the main housing part 260 and the base part 270 are separated.

The surgical suction device 100 could be provided as a single use device, can be adapted for re-use by allowing the device to be sterilised, or a combination of the two. For example, the housing 110 and mixing apparatus 140 could be designed to allow sterilisation, whilst the tip 150 is provided for single use. This is particularly beneficial as tips 150 can be manufactured cheaply, whilst the risk of contamination of a patient from re-use of a sterilised housing 110 is minimal. However, it will be appreciated that any suitable arrangement could be used.

It is noted that another reason for blood and debris collecting in the chamber of a conventional surgical suction device is that there is not necessarily a constant stream of fluid through the device throughout the entire procedure, hence allowing blood to collect and clot, potentially clogging the device.

Accordingly, a further example of a surgical suction device 600 further adapted to at least partially address this issue is shown in FIGS. 6A and 6B. It will be noted that this example is similar to the surgical suction device 200 depicted in FIGS. 2A and 2B, and as such, similar features have been assigned similar reference numerals and will be understood to have similar functionalities.

In this example, the surgical suction device 600 is further provided with an inflow port 690 which connects to the chamber 111. In particular, the inflow port 690 defines a fluid conduit 691 through a wall of the housing 110 to allow a fluid to be drawn into the chamber 111 in use, thereby allowing a constant stream of fluid through the device to be ensured throughout the procedure. It will be appreciated that this will provide a further mechanism to maintain patency within the surgical suction device 600.

As shown in FIGS. 6A and 6B, the inflow port 690 may be provided integrally with the main housing part 260. The inflow port 690 will typically include a connector portion 692 configured to allow a fluid source to be connected to the inflow port 690 via the connector portion 692. In one example, a tubing system (not shown) may be connected to the fluid source at one end and connected to the inflow port 690 using the connector portion 692 at the other end, in order to allow the additional fluid to be supplied from the fluid source. The fluid source may supply any suitable fluid to be drawn into the chamber 111. In some examples the fluid source may supply a sterile water or saline solution.

In any event, the tubing system will allow a flow of the fluid from the fluid source through the surgical suction device 600, with the aim of carrying blood and debris out of the surgical suction device 600 before it clots. Typically, the fluid will be drawn through the tubing system by suction, such that the fluid will supplement the flow of material extracted from the subject via the tip 150, in order to provide a substantially flow of fluid through the chamber 111. The extracted material and the additional fluid can then be mixed in the chamber 111 using the mixing apparatus 140 and the resulting mixture will exit the chamber 111 by being drawn from the surgical suction device 600 via the outlet 130.

It will be appreciated that the above described example uses the suction already being applied to the surgical suction device 600 to draw the fluid into the chamber 111 via the inflow port 690. Accordingly, the fluid does not need to be supplied to the surgical suction device 600 under pressure. In fact, it would usually be preferable to not supply the fluid under pressure as this may result in the undesirable backflow of fluid through the tip 150 towards the surgical site if flow rate of the fluid exceeds the capacity of the suction source to remove the fluid and any extracted material from the chamber or if suction should stop without also stopping the supply of fluid.

By drawing the fluid into the chamber 111 using suction only, the flow rate of the fluid into the chamber 111 will be effectively limited in line with the capacity of the suction to thereby remove the risk of backflow. In some examples, the flow of the fluid into the chamber 111 can also be controlled by providing a valve or other flow control device as part of the inflow port 690 or the connected the tubing system. Such an arrangement may allow the user to select whether or not fluid will be drawn into the chamber 111, such as to allow the chamber 111 to be flushed by the fluid when this may be desirable, and in some examples a valve may be provided which allows the user to vary the flow rate of the fluid as required.

Whilst the above described example provides the inflow port 690 as part of the housing 110, it will be understood that other configurations may be used to provide similar effects. For instance, in some examples the inflow port 690 may be provided as part of the tip 150, which may result in increased patency within at least a portion of the tip 150 in addition to the chamber 111.

In any event, it will be appreciated that the combined mechanisms of the mixing apparatus 140 and the fluid inflow port 690 can help to further combat the problem of clotted blood and debris blocking the suction device surgical 600.

Throughout this specification and claims which follow, unless the context requires otherwise, the word "comprise", and variations such as "comprises" or "comprising", will be understood to imply the inclusion of a stated integer or group of integers or steps but not the exclusion of any other integer or group of integers.

Persons skilled in the art will appreciate that numerous variations and modifications will become apparent. All such variations and modifications which become apparent to persons skilled in the art, should be considered to fall within the spirit and scope that the invention broadly appearing before described.

The claims defining the invention are as follows:

1. A surgical suction device including:
   a) an elongate hollow tip, the tip being for insertion into a surgical site on a subject to allow material to be extracted from the subject and including one or more suction openings for receiving the material from the surgical site;
   b) a housing defining an internal chamber, wherein the tip is removably attached to the housing so that the housing is positioned outside the surgical site and proximate to the subject in use, and wherein the housing defines a handle for the surgical suction device to allow a user to hold the housing outside of the surgical site in use, wherein the chamber is located inside the handle defined by the housing and wherein the chamber includes:
      i) an inlet for receiving the material extracted from the subject via the tip, wherein the tip is coupled to the inlet; and,
      ii) an outlet for coupling the housing to a suction source to allow the material to be extracted from the subject by being drawn through the tip by suction and passing through the chamber from the inlet to the outlet; and,
   c) a mixing apparatus including one or more mixing members positioned inside the chamber for agitating material passing through the chamber from the inlet to the outlet in use to increase the homogeneity of the material and thereby prevent the material clogging from the outlet, wherein the mixing apparatus includes a motor configured to rotate the one or more mixing members, and wherein the motor is positioned inside the chamber along with the mixing members.

2. A surgical suction device according to claim 1, wherein the outlet includes a connector for connection to the suction source.

3. A surgical suction device according to claim 1, wherein the one or more mixing members are at least one of:
   a) radially extending protrusions;
   b) blades; and,
   c) a helical wire.

4. A surgical suction device according to claim 1, wherein the motor is an electric motor and the mixing apparatus includes a battery for electrically powering the motor, and wherein the battery is one of:
   a) provided together with the motor within a sealed housing; and,
   b) positioned outside the chamber and connected to the motor by wiring.

5. A surgical suction device according to claim 4, wherein the surgical suction device includes a controller for controlling the supply of electrical power to the motor from the battery.

6. A surgical suction device according to claim 5, wherein the controller includes a switch positioned outside the housing for manual operation by a user.

7. A surgical suction device according to claim 5, wherein the controller is configured to periodically apply electrical power to the motor.

8. A surgical suction device according to claim 5, wherein the mixing apparatus includes an orientation sensor, the controller being configured to apply power to the motor when the surgical suction device is in a predetermined orientation.

9. A surgical suction device according to claim 1, wherein the housing is formed from a main housing part including the inlet and a base part including the outlet.

10. A surgical suction device according to claim 9, wherein the main housing part and the base part are screwingly connected together.

11. A surgical suction device according to claim 10, wherein the mixing apparatus includes an electrical circuit for powering the motor, the electrical circuit being open except when the main housing part and the base part are screwingly connected together.

12. A surgical suction device according to claim 11, wherein respective portions of the main housing part and the base part each include pairs of electrical contacts which are brought into engagement to close the electrical circuit when the main housing part and the base part are screwingly connected together.

13. A surgical suction device according to claim 9, wherein the main housing part includes an elongate generally cylindrical portion which defines sidewalls of the chamber and forms the handle of the housing.

14. A surgical suction device according to claim 9, wherein the motor is supported inside the chamber using a support structure connected to the base part.

15. A surgical suction device according to claim 1, wherein the surgical suction device includes a support structure attached to the housing and positioned inside the chamber for supporting the mixing apparatus.

16. A surgical suction device according to claim 15, wherein the support structure includes a mounting platform supported inside the chamber by one or more supporting members attached to the housing, the mixing apparatus being mounted on the mounting platform.

17. A surgical suction device according to claim 16, wherein the support structure includes a plurality of supporting members, the supporting members being spaced apart to define gaps for allowing material to pass through the gaps.

18. A surgical suction device according to claim 1, wherein the surgical suction device includes an inflow port for allowing a fluid to be drawn into the chamber via the inflow port in use, and wherein at least one of:
 a) the inflow port is configured to allow a fluid source to be connected to the inflow port to thereby supply the fluid;
 b) the inflow port defines a fluid conduit through a wall of the housing;
 c) the inflow port is formed integrally with the housing; and,
 d) the surgical suction device includes a valve for controlling a flow of fluid via the inflow port.

19. A surgical suction device according to claim 1, wherein the mixing apparatus includes a shaft for mounting the one or more mixing members, the motor rotationally driving the shaft.

\* \* \* \* \*